(12) United States Patent
Takano et al.

(10) Patent No.: US 10,456,110 B2
(45) Date of Patent: Oct. 29, 2019

(54) ULTRASOUND IMAGING APPARATUS

(71) Applicant: HITACHI, LTD., Tokyo (JP)

(72) Inventors: Shinta Takano, Tokyo (JP); Hiroshi Masuzawa, Tokyo (JP); Hiroki Tanaka, Tokyo (JP)

(73) Assignee: HITACHI, LTD., Tokyo (JP)

( * ) Notice: Subject to any disclaimer, the term of this patent is extended or adjusted under 35 U.S.C. 154(b) by 329 days.

(21) Appl. No.: 15/320,050

(22) PCT Filed: Jul. 17, 2014

(86) PCT No.: PCT/JP2014/069110
§ 371 (c)(1),
(2) Date: Dec. 19, 2016

(87) PCT Pub. No.: WO2016/009544
PCT Pub. Date: Jan. 21, 2016

(65) Prior Publication Data
US 2017/0209123 A1 Jul. 27, 2017

(51) Int. Cl.
*A61B 8/00* (2006.01)
*G01S 7/52* (2006.01)
*G01S 15/89* (2006.01)

(52) U.S. Cl.
CPC .............. *A61B 8/4494* (2013.01); *A61B 8/00* (2013.01); *A61B 8/465* (2013.01); *A61B 8/54* (2013.01); *G01S 7/52046* (2013.01); *G01S 7/52085* (2013.01); *G01S 7/52095* (2013.01); *G01S 7/52084* (2013.01); *G01S 15/8915* (2013.01)

(58) Field of Classification Search
CPC .............. G01S 7/52046; G01S 7/52085; G01S 7/52095; G01S 7/52084; G01S 15/8915
See application file for complete search history.

(56) References Cited

U.S. PATENT DOCUMENTS

2010/0022883 A1 1/2010 Satoh

FOREIGN PATENT DOCUMENTS

| JP | S61-135641 | 6/1986 |
|----|------------|--------|
| JP | H06-225883 A | 8/1994 |
| JP | H10-118063 A | 5/1998 |
| JP | 2005-323894 A | 11/2005 |

(Continued)

OTHER PUBLICATIONS

International Search Report and Written Opinion for PCT App No. PCT/JP2014/069110 dated Sep. 2, 2014, 8 pgs.

(Continued)

*Primary Examiner* — Paula J Stice
(74) *Attorney, Agent, or Firm* — Procopio, Cory, Hargreaves & Savitch LLP

(57) ABSTRACT

There is provided an ultrasound imaging apparatus that can reduce vertical stripes even though a transmission interval is widened for high speed imaging. When a receiving unit 1201 receives an instruction to perform a high speed imaging mode, an aperture synthesizing unit 1300 adds a predetermined number (N) of phase outputs obtained from the reflected ultrasonic waves of individual transmission beams at the same received focal points to reduce the occurrence of stripes on an image. In order to generate N phase outputs at each of the received focal points, a control unit 401 finds a necessary number (M) of the reception scanning lines to be set by the reception beam former 603, and notifies the reception beam former 603 of the number.

14 Claims, 16 Drawing Sheets

(56) References Cited

FOREIGN PATENT DOCUMENTS

JP      2010-029374 A    2/2010
WO       2012053345 A1   4/2012

OTHER PUBLICATIONS

Notification of Transmittal of Translation of the International Preliminary Report on Patentability for International Patent Application PCT/JP2014/069110 dated Jan. 26, 2017, 7 pages. The International Bureau of WIPO, Geneva, Switzerland.

FIG. 1
(A) NORMAL IMAGING
UNIDIRECTIONAL TRANSMISSION UNIDIRECTIONAL RECEPTION
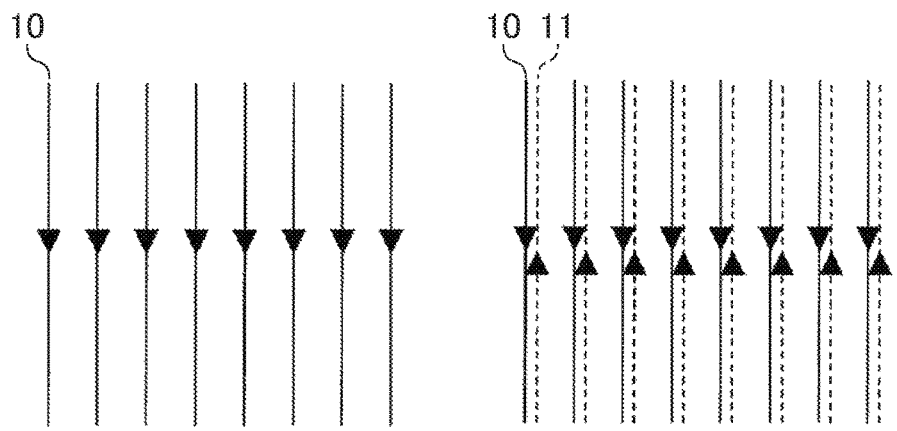
(B) HIGH SPEED IMAGING
UNIDIRECTIONAL TRANSMISSION UNIDIRECTIONAL RECEPTION
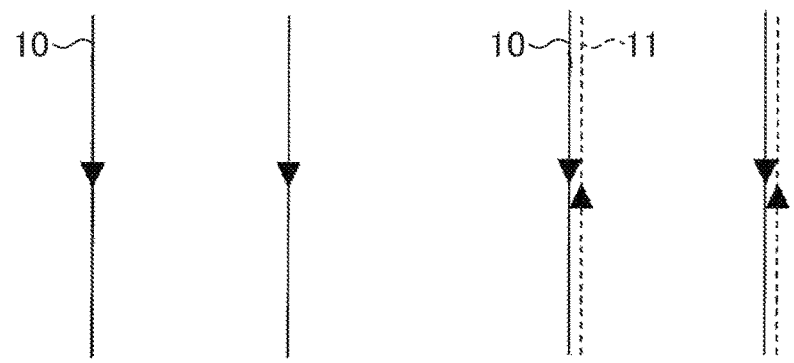
(C) HIGH SPEED IMAGING
UNIDIRECTIONAL TRANSMISSION QUADRI-DIRECTIONAL SIMULTANEOUS RECEPTION
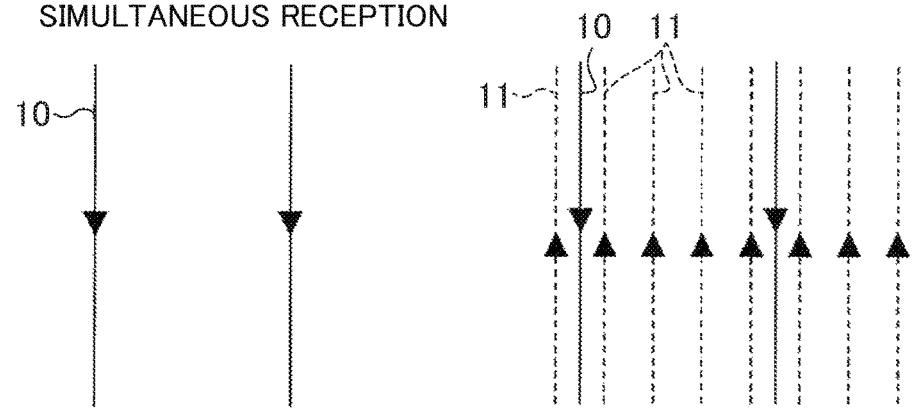

FIG. 2
(A) NORMAL IMAGING 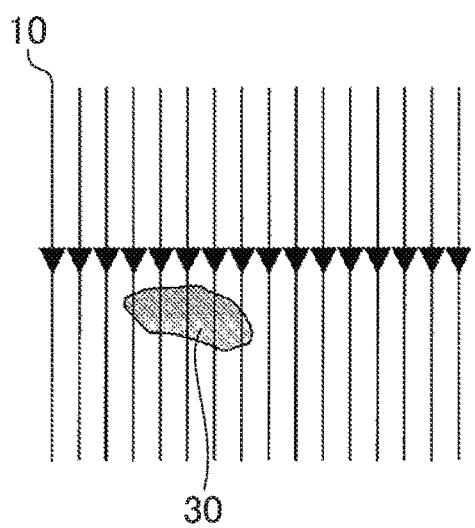
(B) HIGH SPEED IMAGING 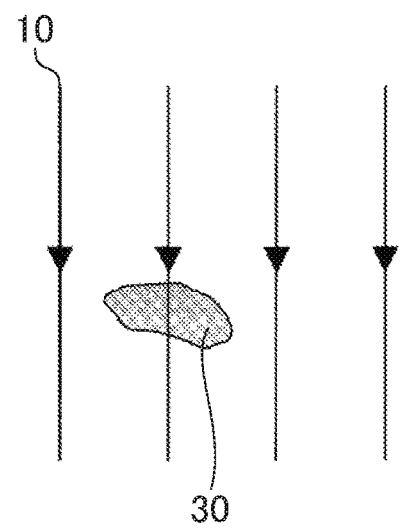

FIG. 5

| NUMBER OF TIMES | | SCANNING LINE NUMBER 1 2 3 4 5 6 7 8 9 10 11 12 13 14 15 16 17 18 19 20 21 22 23 24 25 26 27 28 29 30 31 32 ··· |
|---|---|---|
| 1 | TRANSMISSION | 1 2 3 4 5 6 7 8 9 |
| | RECEPTION | 1 2 3 4 5 6 7 8 9 10 11 12 13 14 15 16 |
| 2 | TRANSMISSION | 5 6 7 8 9 10 11 12 13 |
| | RECEPTION | 5 6 7 8 9 10 11 12 13 14 15 16 17 18 19 20 |
| 3 | TRANSMISSION | 9 10 11 12 13 14 15 16 17 |
| | RECEPTION | 9 10 11 12 13 14 15 16 17 18 19 20 21 22 23 24 |
| 4 | TRANSMISSION | 13 14 15 16 17 18 19 20 21 |
| | RECEPTION | 13 14 15 16 17 18 19 20 21 22 23 24 25 26 27 28 |
| 5 | TRANSMISSION | 17 18 19 20 21 22 23 24 25 |
| | RECEPTION | 17 18 19 20 21 22 23 24 25 26 27 28 29 30 31 32 ··· |
| 6 | TRANSMISSION | 21 22 23 24 25 26 27 28 29 |
| | RECEPTION | 21 22 23 24 25 26 27 28 29 30 31 32 ··· |
| 7 | TRANSMISSION | 25 26 27 28 29 30 31 32 ··· |
| | RECEPTION | 25 26 27 28 29 30 31 32 ··· |
| 8 | TRANSMISSION | 29 30 31 32 ··· |
| | RECEPTION | |
| ··· | | |

○ HIGH SPEED IMAGING MODE

○ HIGH RESOLUTION MODE (b)

WHICH DOUBLE SPEED IS
SET TO IMAGING SPEED?

[    ] X DOUBLE SPEED

FIG. 8

LEVEL OF REMOVAL OF STRIPES

○ HIGH
○ MIDDLE
○ LOW

FIG. 9

RESOLUTION WILL BE REDUCED
FOR ACHIEVING HIGH SPEED
IMAGING. DO YOU ACCEPT IT?

○ Yes
○ No

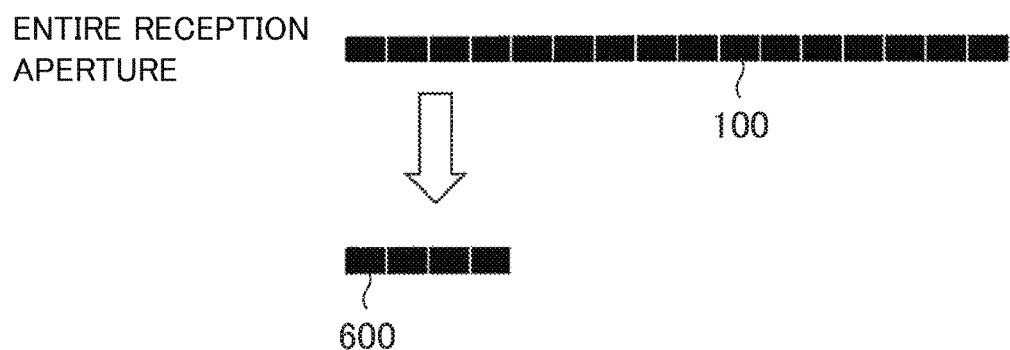
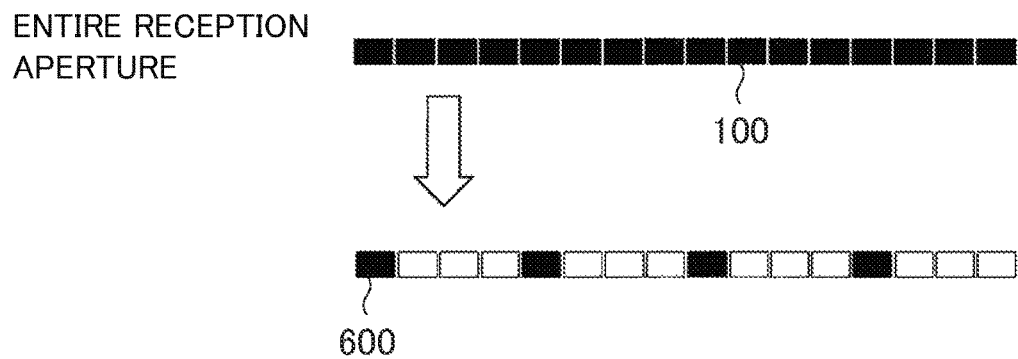

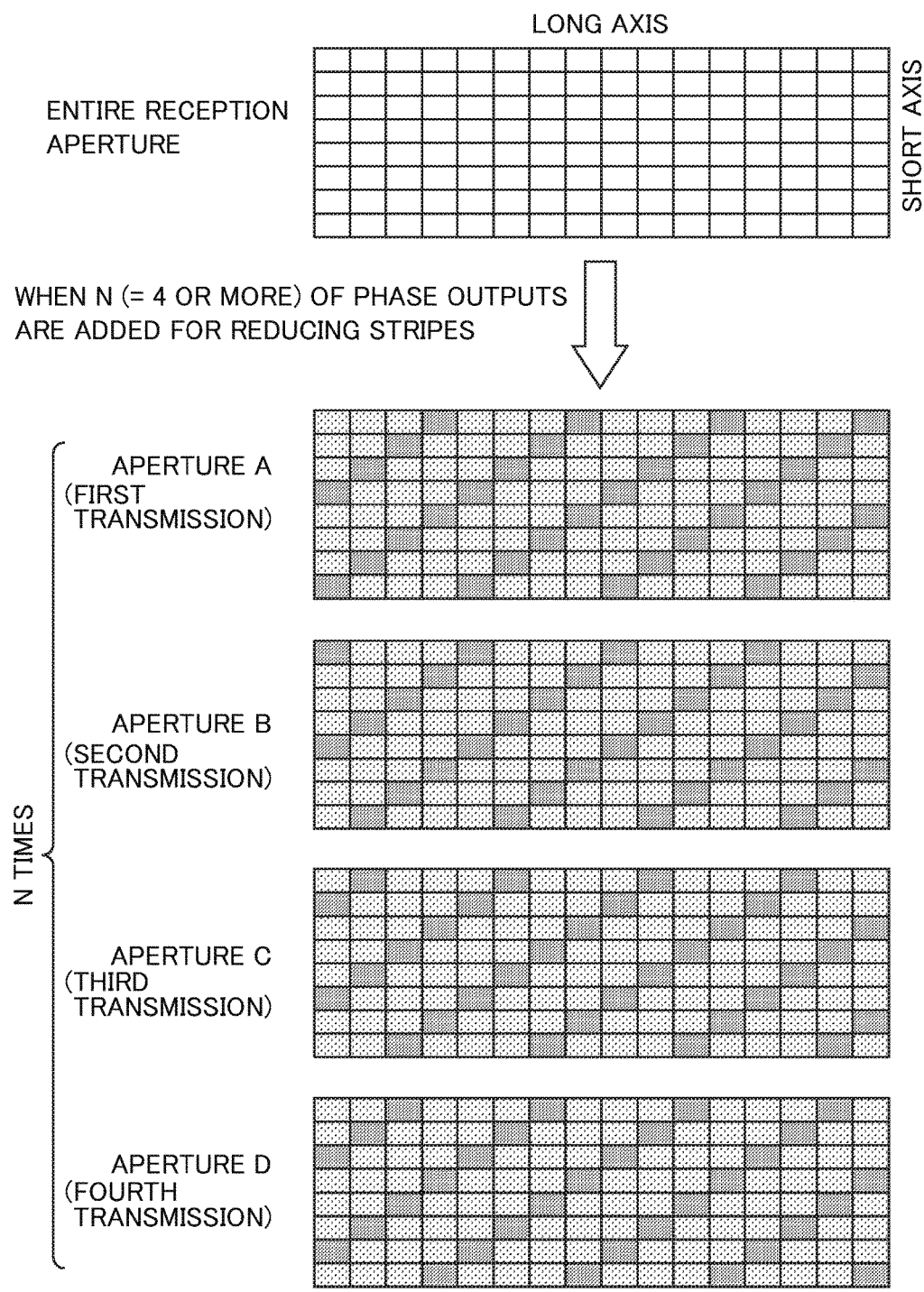

ULTRASOUND IMAGING APPARATUS

CROSS-REFERENCE TO RELATED APPLICATIONS

This application is a U.S. National Stage entry of PCT Application No. PCT/JP2014/069110, filed on Jul. 17, 2014. The contents of the foregoing are incorporated by reference.

TECHNICAL FIELD

The present invention relates to an ultrasound imaging technique in which ultrasonic waves are transmitted from an ultrasound probe to a test object, ultrasonic waves reflected off the interior of the test object are received by the ultrasound probe, and the internal structure of the test object is imaged. More specifically, the present invention relates to a technique of multidirectional parallel simultaneous reception in which a plurality of reception scanning lines are set to one transmission scanning line.

BACKGROUND ART

The ultrasound imaging technique is a technique in which ultrasonic waves, which are inaudible sound waves and are commonly sound waves with frequencies of 20 kHz or more, are used to image the interior of a test object including human bodies in a noninvasive manner. For example, a medical ultrasound imaging apparatus transmits ultrasonic beams from an ultrasound probe to the interior of the body of a test object along transmission scanning lines, and receives echo signals from the interior of the body. A reception beam former generates signals, which are generated by phase-adding the received signals of a plurality of ultrasonic elements, at each of a plurality of received focal points on reception scanning lines. An image processing unit processes these phase outputs to generate an ultrasound image.

In the case where it is desired to form images by high speed imaging on the ultrasound imaging apparatus, limits are imposed on an increase in the operation speed in phase-addition by the reception beam former. Thus, a method is used, in which the number of times of transmission performed in a certain time period is decreased. In this case, in order to maintain the same imaging range (the viewing angle and the depth of the visual field), it is necessary to widen the interval between transmission scanning lines in the imaging range. In order not to extremely degrade the spatial resolution even though the interval between the transmission scanning lines is widened, a technique is known in which multidirectional reception scanning lines are set in parallel with each other to one transmission scanning line (unidirectional transmission multidirectional parallel simultaneous reception).

However, it is known that in the case where multidirectional parallel simultaneous reception is performed as described in Patent Literatures 1 to 4, stripes are produced on an ultrasound image, because the signal level of the phase output at the received focal point is varied between the adjacent reception scanning lines. In order to decrease these stripes, Patent Literature 1 discloses a method in which the phase output is subjected to weighted addition between reception scanning lines. Patent Literature 2 discloses a technique in which the gain of the signal of a reception scanning line is adjusted to remove stripes. Patent Literature 3 discloses a technique in which the position of a transmission beam is shifted for each of the frames of an ultrasound image, and the mean value is calculated between image frames to remove stripes. In a technique of Patent Literature 4, a notch filtering process in the azimuth direction is performed on an ultrasound image to remove stripes.

On the other hand, Patent Literature 5 discloses a method in which some ultrasonic elements are driven to perform the first time transmission and reception, and in the second time transmission, other ultrasonic elements are driven in the same direction to perform transmission and reception, and a reception focusing process (phase-addition) is performed together with the received signals obtained in the first time reception and the received signals obtained in the second time reception. Thus, even though the circuit scale of the ultrasound imaging apparatus is decreased, image quality equivalent to that of an apparatus with a large circuit scale can be secured.

CITATION LIST

Patent Literatures

Patent Literature 1: Japanese Unexamined Patent Application Publication No. Sho61(1986)-135641
Patent Literature 2: Japanese Unexamined Patent Application Publication No. Hei6(1994)-225883
Patent Literature 3: Japanese Unexamined Patent Application Publication No. Hei10(1998)-118063
Patent Literature 4: Japanese Unexamined Patent Application Publication No. 2005-323894
Patent Literature 5: Japanese Unexamined Patent Application Publication No. 2010-29374

SUMMARY OF INVENTION

Technical Problem

The techniques of Patent Literatures 1 to 4 can reduce stripes to some extent. However, the number of times of transmission to obtain an image is decreased to some extent or more in order to further increase speed, no stripes can be eliminated. Patent Literature 5 has no description on stripes. The technique of Patent Literature 5 can eliminate no stripes.

For example, FIG. 1(A) is a diagram illustrative of unidirectional transmission unidirectional reception, in which for one transmission beam 10, one reception scanning line (in the following, also referred to as a received beam) 11 is generated in nearly the same direction as the direction of the transmission beam 10. FIG. 1(B) is a diagram illustrative of the transmission beam 10 and the received beam 11 in unidirectional transmission unidirectional reception in the case where the transmission interval is widened. In FIG. 1(B), since the number of times of transmission of the transmission beam 10 for obtaining one ultrasound image is small, high speed imaging is performed. However, the density of the received beams 11 is also coarse, degrading the azimuth resolution of ultrasound images. FIG. 1(C) is a diagram illustrative of unidirectional transmission multidirectional parallel simultaneous reception. In FIG. 1(C), the number of times of transmission of the transmission beam 10 for obtaining one ultrasound image is small. Thus, high speed imaging can be implemented, and the density of the received beams 11 is equivalent to that in FIG. 1(A), allowing the resolution to be maintained. However, in unidirectional transmission multidirectional parallel simultaneous reception as in FIG. 1(C), vertical stripe artifacts are produced on ultrasound images.

The inventors investigated various causes to produce stripes in unidirectional transmission multidirectional parallel simultaneous reception. It is thought that one of causes of stripes is the sound field distribution of transmission beams. The amplitude of the ultrasonic wave of the transmission beam is great near the transmission focal point, and becomes small apart from the transmission focal point to the outer side of the azimuth direction. As a result, the reflected wave of the transmission beam also has a similar amplitude distribution. The amplitude of a parallel simultaneous reception beam to be generated is relatively large near the transmission focal point, and becomes small apart to the outer side of the azimuth direction. Thus, for example, in the case where four received beams are formed as the transmission focal point is the center, two received beams in the center have high sensitivity and two received beams on the outer sides have low sensitivity. Consequently, a distribution is formed in order from the left of the four received beams, low, high, high, and low sensitivities. This distribution is also produced on four received beams of the adjacent transmission beam. Thus, in the entire ultrasound image, changes in sensitivity are repeatedly produced for each received beam (each reception scanning line), low, high, high, and low sensitivities, low, high, high, and low sensitivities, and so on. This distribution appears as vertical stripes on the ultrasound image.

For other causes, the difference in the luminance value (the amplitude of the ultrasonic wave) between adjacent transmission beams is thought. A plurality of received beams obtained from the same transmission beam have close luminance values. However, the adjacent transmission beams have different luminance values. Thus, a plurality of received beams set to a transmission beam and pluralities of received beams adjacent to the transmission beam have different luminance values. Consequently, differences in the luminance values occur between the received beams of different transmission beams, which appear as stripes on the ultrasound image.

Assuming that the sound field distribution of the transmission beams is dominant in the causes of stripes, it is thought that stripes are observed only near the transmission focal point. However, from the close observation of an ultrasound image formed by high speed imaging in unidirectional transmission multidirectional parallel simultaneous reception, stripes are observed on the entire image. Thus, it is thought that a main cause of stripes is differences in the luminance values between the adjacent transmission beams, not the sound field distribution of the transmission beams.

Therefore, the inventors investigated reasons why differences in luminance values occur between the adjacent transmission beams. This will be described with reference to FIGS. 2(A) and 2(B) and FIG. 3. FIG. 2(A) is a schematic diagram of normal imaging with dense transmission intervals. FIG. 2(B) is a schematic diagram of high speed imaging in the case of coarse transmission intervals. In FIG. 2(A) with dense transmission intervals, five transmission beams 10 pass through a reflecting object 30, whereas in high speed imaging with coarse transmission intervals, only one transmission beam 10 passes through the reflecting object 30 as illustrated in FIG. 2(B). In other words, in FIG. 2(B), the sound wave reflection states of the sound wave propagation paths of the adjacent transmission beams 10 are greatly varied depending on whether the transmission beams 10 pass through the reflecting object 30, causing differences in luminance values. The presence of the reflecting object 30 as well as the absorption of the ultrasonic wave of a substance in the propagation path, transmission directivity, and the like are also factors to cause differences in the luminance values between the sound wave propagation paths.

Next, the inventors investigated positions at which stripes are produced because of differences in the luminance between adjacent transmission beams. This will be described with reference to FIG. 3. In an example in FIG. 3, four received beams 24 are generated for a transmission beam 20 on the left side, four received beams 25 are generated for a transmission beam 21 in the center, and four received beams 26 are generated for a transmission beam 22 on the right side. As illustrated in FIG. 3, in the case where a reflecting object 30 is present only on the sound wave propagation path of the transmission beam 21 in the center, the transmission beam 21 having passed through the reflecting object has a luminance value smaller than the luminance values of the transmission beams 20, 22 on both sides. Thus, the luminance values of the four received beams 25 in the center are smaller than the luminance values of the received beams 24, 26 on both sides. Consequently, vertical stripes appear on a boundary 27 between the four received beams 25 in the center and the left received beam 24 and on a boundary 27 between the four received beams 25 in the center and the right received beam 26 (in FIG. 3, the boundary 27 between received beams 25-1 and 24-4 and the boundary 27 between received beams 25-4 and 26-1).

An object of the present invention is to provide an ultrasound imaging apparatus that can reduce vertical stripes even though a transmission interval is widened for high speed imaging.

In order to achieve the object, in an ultrasound imaging apparatus according to the present invention, in the case where a receiving unit receives an instruction to perform a high speed imaging mode, an aperture synthesizing unit adds a predetermined number (N) of phase outputs obtained from the reflected ultrasonic waves of individual transmission beams at the same received focal points to reduce the occurrence of stripes on an image. In order to generate N phase outputs at each of the received focal points, a control unit finds a necessary number (M) of reception scanning lines, which a reception beam former has to set, and notifies the reception beam former of the number.

According to the ultrasound imaging apparatus of the present invention, even though a transmission interval is widened for high speed imaging, vertical stripes can be reduced, and an ultrasound image of high definition can be obtained.

BRIEF DESCRIPTION OF DRAWINGS

FIG. 1(A) is a diagram illustrative of unidirectional transmission unidirectional reception in normal imaging; FIG. 1(B) is a diagram illustrative of unidirectional transmission unidirectional reception in high speed imaging; and FIG. 1(C) is a diagram illustrative of unidirectional transmission multidirectional parallel simultaneous reception in high speed imaging.

FIG. 2(A) is a diagram illustrative of the relationship between space intervals for transmission in normal imaging and a reflecting object 30; and FIG. 2(B) is a diagram illustrative of the relationship between space intervals for transmission in high speed imaging and the reflecting object 30.

FIG. 5 is an illustration of the positions of transmission scanning lines and reception scanning lines set in the ultrasound imaging apparatus according to the first embodiment.

FIG. 7(a) is an illustration of an exemplary screen for selecting imaging modes displayed in Step 100 in FIG. 6; and FIG. 7(b) is an illustration of an exemplary screen for receiving imaging speed displayed in Step 101 in FIG. 6.

FIG. 8 is an illustration of an exemplary screen for selecting the level of removal of stripes displayed in Step 103 in FIG. 6.

FIG. 9 is an illustration of an exemplary screen for displaying a decrease in resolution displayed in Step 108 in FIG. 6.

FIG. 10 is an illustration of a comparative example for selecting ultrasonic elements.

FIG. 11 is an illustration of a comparative example for selecting ultrasonic elements.

FIG. 18 is an illustration of an example of a two-dimensional ultrasonic element array and element selection patterns usable in an embodiment.

DESCRIPTION OF EMBODIMENTS

In the following, according to an embodiment of the present invention the ultrasound imaging apparatus will be described.

First Embodiment

Figure 3:
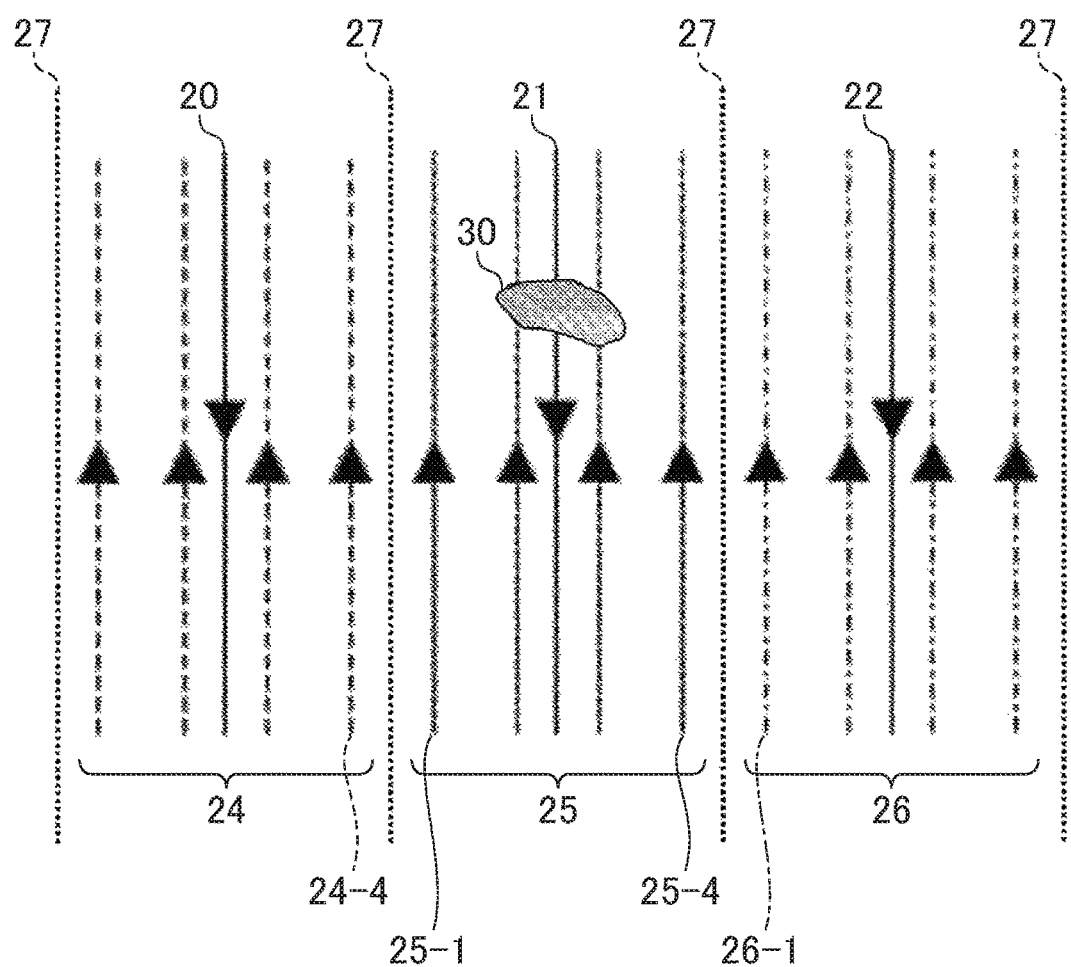
FIG. 3 is an illustration of a boundary 27 where stripes are produced because of differences in the luminance between a plurality of transmission beams.
Figure 4:
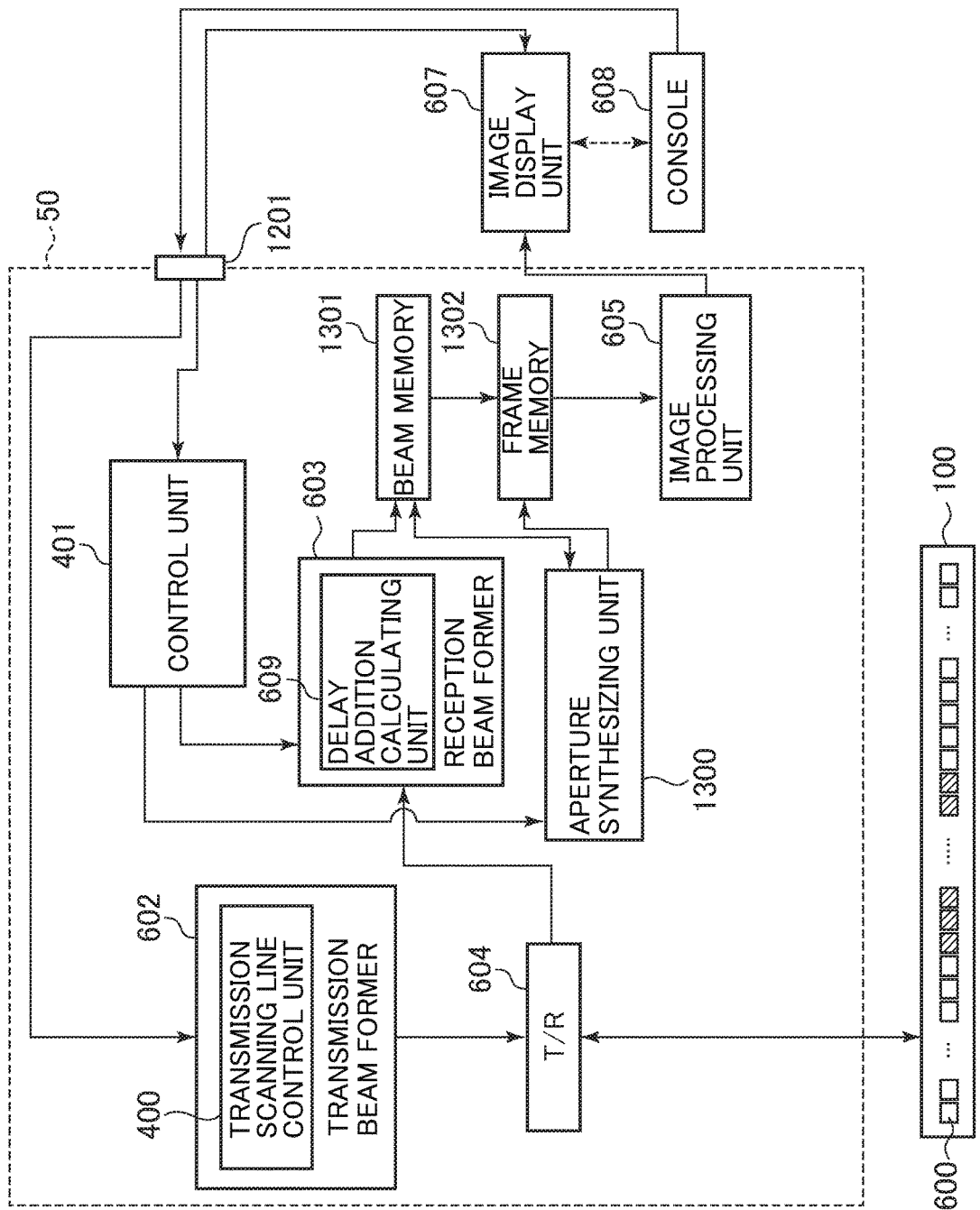
FIG. 4 is a block diagram of the configuration of an ultrasound imaging apparatus according to a first embodiment.

As illustrated in FIG. 4, an ultrasound imaging apparatus according to this embodiment includes an ultrasonic element array 100, a transmission beam former 602, a reception beam former 603, an aperture synthesizing unit 1300, a receiving unit (1201) that receives an instruction to perform a high speed imaging mode from an operator, and a control unit 401.

The ultrasonic element array 100 is configured in which a plurality of ultrasonic elements 600 that transmit ultrasonic waves to the imaging area of a test object and receives ultrasonic waves reflected off the test object is arrayed along a predetermined direction. The transmission beam former 602 sequentially transmits signals causing transmission beams to be transmitted from the ultrasonic element array 100 along a plurality of transmission scanning lines set in the imaging area of the test object at a predetermined transmission timing. The reception beam former 603 sets a plurality of reception scanning lines for each transmission beam. The reception beam former 603 then generates phase outputs (received beams), which the received outputs of the plurality of ultrasonic elements 600 are phased and added, at a plurality of received focal points on the respective reception scanning lines. The aperture synthesizing unit 1300 adds a plurality of phase outputs obtained from the reflected ultrasonic waves of the individual transmission beams at the same received focal points and generates an image of the imaging area.

In the case where the receiving unit 1201 receives an instruction to perform a high speed imaging mode from the operator, the transmission beam former 602, the aperture synthesizing unit 1300, and the control unit 401 are operated as below. The transmission beam former 602 sequentially transmits signals causing transmission beams to be transmitted along transmission scanning lines at intervals corresponding to the imaging speed in the high speed imaging mode. For example, as illustrated in FIG. 5, in the case where the imaging speed in the high speed imaging mode is the speed four times the speed in normal imaging (one reception scanning line is set to one transmission), the transmission beam former 602 sets transmission scanning lines at a ratio of one to four scanning lines at intervals used in normal imaging, and then sequentially transmits signals causing transmission beams to be transmitted along the transmission scanning lines.

The aperture synthesizing unit 1300 sets the number of phase outputs to be added for each received focal point to a predetermined addition number (N) that reduces the occurrence of stripes on an image. The addition number (N) is set to the number that can reduce stripes (e.g. N=4), which is found in advance.

The control unit 401 finds a necessary number (M) of the reception scanning lines, which the reception beam former 603 has to set, in order to generate the addition number (N) of phase outputs for each received focal point, and informs the reception beam former 603 of the found necessary number (M) of the reception scanning lines. The reception beam former 603 sets M lines of the reception scanning lines for each reception. For example, in an example in FIG. 5, M (=16) lines of the reception scanning lines is set for each reception to one transmission, and N (=4) lines of the reception scanning lines are overlapped with each other at a scanning line number 13 and subsequent numbers.

More specifically, in the example in FIG. 5, the imaging speed is quadruple speed, in which the transmission beam former 602 sets the transmission scanning lines at positions every four scanning line numbers. In order to achieve the addition number N (=4), the control unit 401 finds that it is necessary to provide M (=16) lines of the reception scanning lines, and sets the number to the reception beam former 603. Thus, the transmission beam former 602 sets the transmission scanning line at the position between scanning line numbers 8 and 9 in the first time transmission for transmission. In the second time transmission, the transmission beam former 602 sets the transmission scanning line at the position between scanning line numbers 12 and 13 four scanning lines apart from the position of the transmission scanning line in the first time transmission. In the third time transmission, the transmission beam former 602 sets the transmission scanning line at the position between scanning line numbers 16 and 17 four scanning lines apart from the position of the transmission scanning line in the second time transmission. In the fourth time transmission, the transmission beam former 602 sets the transmission scanning line at the position between scanning line numbers 20 and 21 four scanning lines apart from the position of the transmission scanning line in the third time transmission. Thus, high speed imaging can be achieved, which is four times the speed in the case where one transmission is performed for each scanning line number. In order to set M (=16) lines of the reception scanning lines to each scanning line number for each transmission, the reception beam former 603 sets the reception scanning lines to scanning line numbers 1 to 16 in the first time reception, the scanning line numbers 5 to 20 in the second time reception, scanning line numbers 9 to 24 in the third time reception, and scanning line numbers 13 to 28 in the fourth time reception. Thus, four reception scanning lines are formed being overlapped with each other at the same scanning line numbers in the scanning line number 13 and subsequent numbers. Consequently, at the received focal points on the overlapped reception scanning lines, N (=4) of phase outputs obtained in the individual transmissions can be added at the aperture synthesizing unit 1300. Thus, the number of the reception scanning lines necessary to reduce stripes can be secured, and the necessary addition number N of phase outputs can be added for synthesizing, while performing high speed imaging. Accordingly, stripes can be reduced.

In the description above, the case is described where in order to reduce stripes, the addition number N of the phase outputs to be added at the aperture synthesizing unit 1300 is a predetermined number (e.g. N=4). However, the level of reducing stripes is changed depending on the value of the addition number N. Thus, a configuration may be possible in which the receiving unit (1201) receives the level of reducing stripes desired by the operator. In this case, the control unit 401 sets the addition number N corresponding to the level of reducing stripes received at the receiving unit (1201). The control unit 401 finds the necessary number M of the reception scanning lines corresponding to the addition number N. For example, a configuration is possible in which the relationship between a plurality of types of addition numbers N and the respective levels of reducing stripes is determined in advance and formed in a table, for example, and the control unit 401 finds the addition umber N corresponding to the level of reducing stripes set by the operator based on this relationship (table).

On the other hand, in the ultrasound imaging apparatus according to the embodiment, in order to achieve high speed imaging, the transmission time interval between the transmission beams is set similarly to the previously existing transmission time interval, and the space interval of the transmission beams is widened. To this end, the reception beam former 603 has to complete the arithmetic operation for calculating the phase outputs at each received focal point on the necessary number (M lines) of the reception scanning lines within the transmission time interval between the transmission beams. Because of this, depending on the operation speed determined by the scale of the arithmetic circuit of the reception beam former 603, limitations are imposed on the number of the reception scanning lines that can be operated within the transmission time interval. Thus, the range of settable imaging speed for high speed imaging has the upper limit depending on operation speed.

The control unit 401 can achieve much higher speed imaging by performing control below. In other words, a maximum number (K) of the reception scanning lines is found in advance by calculation or experiment. The maximum number (K) is the number that can be operated within the transmission time interval in the case of arithmetic operation using the outputs of all the ultrasonic elements 600. In the case where the necessary number (M) of the reception scanning lines is the number (K) or less, the control unit 401 causes the reception beam former 603 to generate outputs using the outputs of all the ultrasonic elements 600 of the ultrasonic element array 100. On the other hand, in the case where the necessary number (M) of the reception scanning lines exceeds the predetermined number (K), it is not possible to operate the phase outputs of all the reception scanning lines within the transmission time interval using all the ultrasonic elements 600 for arithmetic operation. Thus, the control unit 401 finds the number of the ultrasonic elements 600 usable for generating the phase outputs at the received focal points of the necessary number (M) of the reception scanning lines within the transmission time interval of the transmission beam based on the operating capability of the reception beam former. The control unit 401 then causes the reception beam former 603 to generate the phase outputs using the received outputs of the found number of the ultrasonic elements 600. Thus, the number of the ultrasonic elements 600 used for operating the phase outputs can be reduced. Consequently, the load of operating the reception beam former 603 is reduced. Even in the case where high speed imaging exceeding the operating capability is set, the phase outputs are calculated on the necessary number (M) of the reception scanning lines within the transmission time interval, allowing high speed imaging to be achieved.

For example, the control unit 401 has a table showing the relationship between the necessary number (M) of the reception scanning lines, the transmission interval of the transmission beam, and the number of the usable ultrasonic elements, which are found in advance. With reference to this table, the control unit 401 can find the number of usable ultrasonic elements.

Note that, in the case where the necessary number (M) of the reception scanning lines exceeds the predetermined number (K) and the number of the ultrasonic elements 600 used for operating the phase outputs is to be decreased, the resolution of an ultrasound image to be generated is likely to be decreased below the resolution of an ultrasound image to be generated using all the ultrasonic elements 600. Thus, the control unit 401 may display an indication that informs the operator of the possibility of a decrease in the resolution on the display device.

In the following, the ultrasound imaging apparatus according to the embodiment will be described more in detail. Note that, the present invention is not limited to embodiments below.

As illustrated in FIG. 4, an ultrasound imaging apparatus 50 according to the embodiment includes the ultrasonic element array (the probe array) 100, the transmission beam former 602, the reception beam former 603, the aperture synthesizing unit 1300, the control unit 401, and the receiving unit (here, an input/output port 1201), and also includes an image processing unit 605, a beam memory 1301, a frame memory 1302, and a transmission/reception switching unit (T/R) 604.

The input/output port 1201, which is the receiving unit, is connected to a console 608, and receives a selection of the high speed imaging mode or the normal imaging mode, a selection of the imaging speed (X double speed is selected for imaging) in the case of the high speed imaging mode, and a selection of the level of reducing stripes.

The transmission beam former 602 includes a transmission scanning line control unit 400. After the input/output port 1201 receives a selection of the high speed imaging mode or the normal imaging mode and a selection of the imaging speed through the console 608, the transmission scanning line control unit 400 determines the interval between the transmission scanning lines for achieving the imaging speed based on an equation or a table found in advance. The transmission scanning line control unit 400 also sets transmission focal points. The transmission beam former 602 transmits signals causing transmission beams to be transmitted along the transmission scanning lines determined at the transmission scanning line control unit 400.

The reception beam former 603 includes a delay addition calculating unit 609. The delay addition calculating unit 609 delays and phases the received signals of ultrasonic waves reflected off the inside of the test object received at the plurality of ultrasonic elements 600 of the ultrasonic element array 100 and then adds the signals. The delay addition calculating unit 609 includes an arithmetic circuit that can perform time division arithmetic processing, which can delay and add signals at received focal points of a plurality of reception scanning lines at almost the same time instant for one transmission and can generate phase outputs. The number of the reception scanning lines set for one transmission is set by the control unit 401. The phase output for each reception scanning line generated by the reception beam former 603 is stored on the beam memory 1301.

The aperture synthesizing unit 1300 reads the phase outputs of the reception scanning lines obtained in one transmission and the phase outputs (N phase outputs in total) of the reception scanning lines obtained in other transmissions out of the beam memory 1301, and adds and synthesizes them at each of the same received focal points. The addition number N is set by the control unit 401.

The phase output synthesized by the aperture synthesizing unit 1300 is stored on the frame memory 1302. The image processing unit 605 reads the synthesized phase output stored on the frame memory 1302 to generate an image (an ultrasound image). The image is displayed on the image display unit 607.

Figure 6:
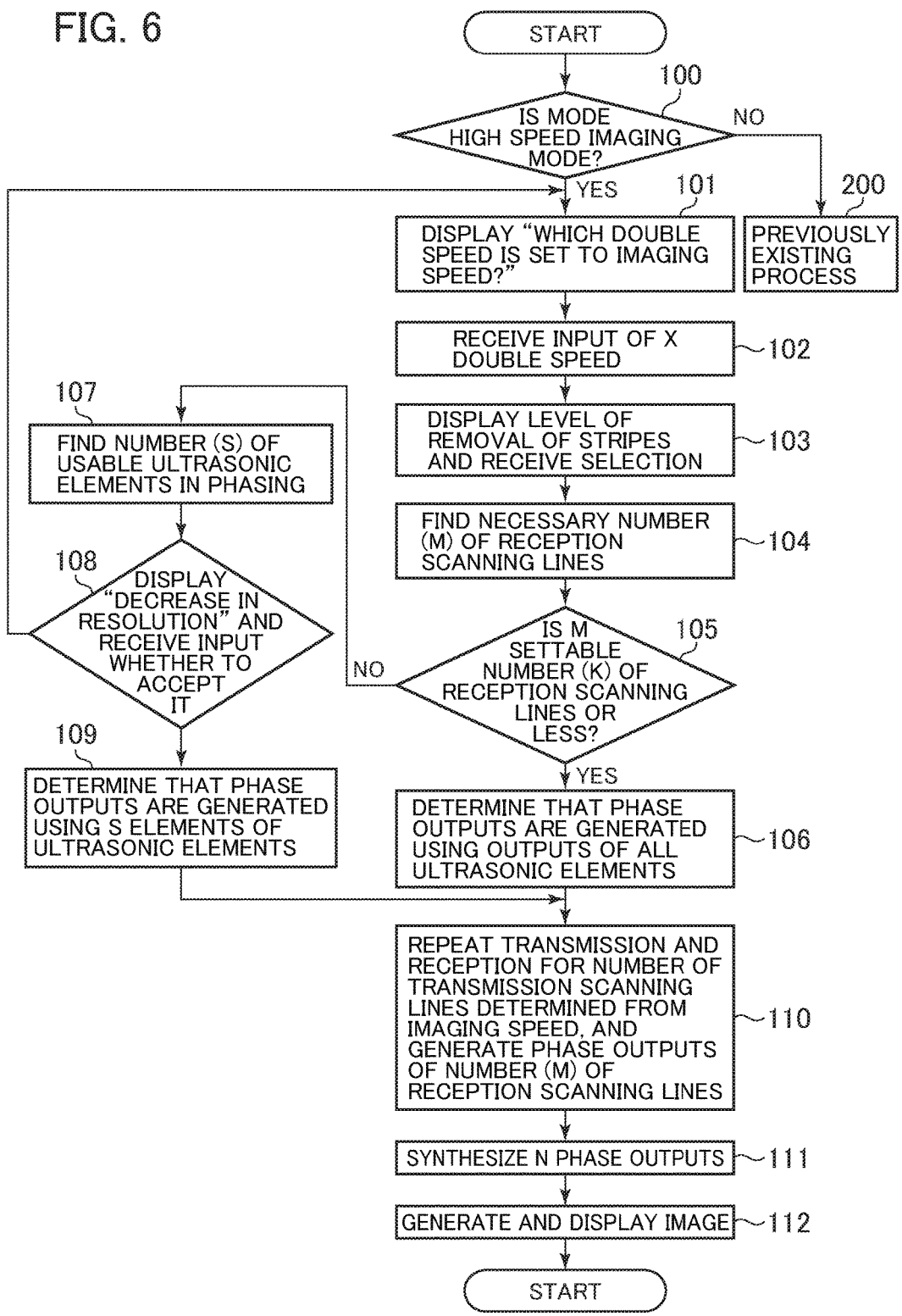
FIG. 6 is a flowchart of the operation of the ultrasound imaging apparatus according to the first embodiment.

In the following, referring to a flowchart in FIG. 6, the operation of the components will be further described.

As illustrated in FIG. 7(a), the control unit 401 first displays a screen for receiving the setting of the imaging mode on the image display unit 607 through the input/output port 1201. In the case where the operator selects the high speed imaging mode through the console 608, as illustrated in FIG. 7(b), the control unit 401 sets a screen for receiving the imaging speed, and receives the imaging speed (Steps 100 to 102). For a method of receiving the imaging speed, the operator may input numerical characters indicating X double speed of typical imaging speed, in which one reception scanning line is set for each transmission scanning line as a screen in FIG. 7(b), and other various methods may be used. For example, a configuration may be possible in which selectable values of imaging speed are displayed and the operator selects one of them, or in which the operator inputs which way of transmission is desired for generating one image.

Note that, in the case where the operator selects a high resolution mode in Step 100, a previously existing low speed imaging operation is performed (Step 200).

Subsequently, as illustrated in FIG. 8, the control unit 401 displays a screen for receiving the setting of the level of reducing stripes (the level of removal of stripes) from the operator on the image display unit 607, and receives a selection by the operator (Step 103). In an example in FIG. 8, the operator selects the level of reducing stripes from three stages high, middle, and low levels. These three stages correspond to the addition number (N) of phase outputs added by the aperture synthesizing unit 1300. At "high", N=5, at "middle", N=4, and at "low", N=3. The value of N is a value found by experiment in advance. A first table of the correspondence between the value of N and the level of reducing stripes is in advance stored on a storage unit in the control unit 401.

The storage unit in the control unit 401 stores a second table showing the relationship between the imaging speed, the addition number (N) of the phase outputs, and the necessary number (M) of the reception scanning lines for each transmission, which are found in advance by calculation.

The control unit 401 finds the value of the addition number (N) of phase outputs corresponding to the level of removal of stripes received in Step 103 with reference to the first table. In order to achieve the found addition number (N) of phase outputs and the imaging speed received in Step 102, the control unit 401 finds the necessary number of reception scanning lines (M lines) with reference to the second table (Step 104).

The control unit 401 further determines whether the necessary number (M) of the reception scanning lines found in Step 104 is the number (K) of the settable reception scanning lines found in advance or less (Step 105). The number K is the maximum number of the reception scanning lines calculable within the transmission time interval of the transmission beam former 102, which is preset corresponding to the operation speed (the arithmetic circuit scale) of the reception beam former 603.

In the case where the necessary number of the reception scanning lines (M lines) found in Step 104 is the number K or less, the process goes to Step 106, and the control unit 401 sets an instruction on the reception beam former 603 to generate phase outputs using all the ultrasonic elements 600 of the ultrasonic element array 100 (Step 106).

The process goes to Step 110, and the control unit 401 causes the transmission beam former 602 and the reception beam former 603 to perform transmission and reception. Specifically, the transmission scanning line control unit 400 in the transmission beam former 602 calculates the number of the transmission scanning lines (or the space interval of the transmission scanning line) in order to achieve the imaging speed received in Step 102, and sets the transmission scanning lines. For an example, the storage unit in the transmission scanning line control unit 400 stores a table that defines the relationship between the imaging speed and the space interval of the transmission scanning line, which are found in advance by calculation. The transmission scanning line control unit 400 finds the space interval of the transmission scanning line corresponding to the imaging speed set by the operator in Step 102 with reference to the table. The transmission scanning lines are set at this interval. For example, as illustrated in FIG. 5, in order to achieve quadruple-speed imaging, the transmission scanning lines are set apart every four predetermined scanning lines. On the other hand, the control unit 401 sets the number (M lines) of the reception scanning lines found in Step 104 to the reception beam former 603. As illustrated in FIG. 5, the reception beam former 603 sets M (=16) lines of the reception scanning lines as a predetermined position (e.g., the transmission scanning line) is the center. The transmission beam former 602 then transmits the signals causing the transmission beams to be transmitted from the ultrasonic element array 100 along the set transmission scanning lines at the time interval determined in advance. All the ultrasonic elements 600 receive the reflected ultrasonic waves of the test object in each transmission. The delay addition calculating unit 609 of the reception beam former 603 generates phase outputs at the received focal points on M lines of the reception scanning lines using the outputs of all the ultrasonic elements 600 (Step 110). Thus, the phase outputs of M lines of the reception scanning lines for one transmission are generated almost at the same time. The generated phase outputs are stored on the beam memory 1301. This process is repeated until all transmissions are finished.

The aperture synthesizing unit 1300 receives the addition number (N) corresponding to the level of reducing stripes, which has been received from the control unit 401 in Step 103. The aperture synthesizing unit 1300 then reads N phase outputs at the same received focal points out of the beam memory 1301, and adds the phase outputs. The added phase outputs are stored on the frame memory 1302 (Step 111).

The image processing unit 605 reads the added phase outputs on all the received focal points out of the frame memory 1302, generates an image, and displays the image on the image display unit 607 (Step 112).

As described above, in the embodiment, the number of the reception scanning lines necessary to achieve aperture synthesis in the addition number (N) necessary to reduce stripes can be found suitable for the imaging speed set by the operator. Accordingly, stripes can be reduced while performing high speed imaging.

Note that, in Step 105, under the conditions in which the number (M) of the reception scanning lines found in Step 104 exceeds the number (K) of the settable reception scanning lines, when the phase outputs are generated using the outputs of all the ultrasonic elements 600, the arithmetic operation is not finished within the transmission time interval of the transmission beam by the operating capability of the reception beam former 603. Therefore, in the embodiment, the number of the ultrasonic elements 600 used for generating the phase outputs is decreased to reduce the amount of arithmetic operation, and phase outputs are generated within the transmission time interval of the transmission beam.

In other words, in the case where the number (M) of the reception scanning lines found in Step 105 exceeds the settable number (K), the process goes to Step 107, and a number (S) of the ultrasonic elements 600 usable for generating the phase outputs within the transmission time interval is found suitable for the number (M) of the reception scanning lines found in Step 104. Specifically, the storage unit in the control unit 401 stores a third table that shows the relationship between the number (S) of the usable ultrasonic elements 600 and the number (M (>K)) of the reception scanning lines, which are found in advance by calculation or experiment taking into account of the operation speed of the reception beam former 603. The control unit 401 finds the number (S) of the usable ultrasonic elements 600 corresponding to the number (M) of the reception scanning lines found in Step 104 with reference to the third table.

In Step 108, in the case where the number of the ultrasonic elements 600 used for operating the phase outputs is decreased, the control unit 401 displays a screen on the image display unit 607 for asking the operator whether to accept reduction in resolution lower than the resolution in the case of using all the ultrasonic elements 600 as in FIG. 9. In the case where the operator selects "Yes (reduction is acceptable)" through the console 608, the process goes to Step 109. In Step 109, the reception beam former 603 receives a decreased number (S) of the ultrasonic elements 600 from the control unit 401, and determines the arrangement of the ultrasonic elements 600 for use based on a predetermined pattern.

The process goes to Step 100, and the delay addition calculating unit 609 uses the outputs of the determined ultrasonic elements 600 to generate the phase outputs for the respective reception scanning lines. Since the number (S) of the ultrasonic elements 600 is decreased, the phase outputs for all the reception scanning lines can be calculated within the transmission time interval even though the number of the reception scanning lines (M) exceeds the number K. This process is repeated until all transmissions are finished. The process goes to Steps 111, 112, N phase outputs are added at the received focal points, and an image is generated and displayed.

Note that in Step 108, in the case where the operator selects "No (reduction is not acceptable)" through the console 608, the process returns to Step 101. The resetting of the imaging speed or the level of reducing stripes is received (Steps 102, 103), and the necessary number (M) of the reception scanning lines is again found. As described above, the resetting of the imaging speed or the level of reducing stripes is received, allowing imaging to be performed at imaging speed or the level of reducing stripes with no reduction in resolution.

As described above, in the ultrasound imaging apparatus according to the embodiment, the number (M) of the reception scanning lines necessary to achieve aperture synthesis in the addition number (N) necessary to reduce stripes is found suitable for the imaging speed set by the operator. Thus, stripes can be reduced while performing high speed imaging. The number (S) of the ultrasonic elements used for generating the phase outputs can be decreased in priority of imaging speed and reduction in stripes. Accordingly, higher speed imaging can also be achieved without changing the operation speed of the reception beam former 603.

Note that, in the embodiment above, in Steps 104, 107, the necessary number (M) of the reception scanning lines and the number (S) of the ultrasonic elements usable in phasing are found with reference to predetermined tables. However, the embodiment is not limited to these tables. It is of course also possible to calculate the numbers M and S by arithmetic operation based on predetermined equations.

Second Embodiment

A second embodiment of the present invention will be described. In the second embodiment, in the case where the necessary number (M) of the reception scanning lines exceeds the number K in Step 105 and the number of the ultrasonic elements used for operating the phase outputs is decreased to the number S in Step 107 in the first embodiment, a control unit 401 determines the arrangement of ultrasonic elements 600 used by a reception beam former 603 for each reception in such a manner that all the ultrasonic elements of an ultrasonic element array 100 are used by the reception beam former 603 for one time or more in reception for N times of transmission equal to the addition number (N). In generating N phase outputs to be added by aperture synthesis for reducing stripes, all the ultrasonic elements 600 are used by the reception beam former 603 for one time or more. Thus, artifacts can be reduced.

Alternatively, in reception for N times of transmission equal to the addition number (N), the control unit 401 can also determine the arrangement of the ultrasonic elements for use in such a manner that a predetermined number of ultrasonic elements among all the ultrasonic elements of the ultrasonic element array are used by the reception beam former for one time or more. Thus, the artifacts can be reduced while further reducing the number of the ultrasonic elements 600 for use.

In the first embodiment, in Step 109, the arrangement of S elements of the ultrasonic elements 600 used for generating phase outputs is determined based on a predetermined pattern. However, the arrangement of the ultrasonic elements 600 is important to prevent artifacts. For example, as illustrated in FIG. 10, when S elements (in FIG. 10, S=4) of the ultrasonic elements are selected from the end of the ultrasonic element array 100 without changing the size of the ultrasonic element 600, the reception aperture of the ultrasonic element array 100 is narrowed. This causes the azimuth resolution to be degraded, and also causes the SN ratio to be decreased. On the other hand, as illustrated in FIG. 11, when S elements of the ultrasonic elements 600 are selected at certain intervals (in FIG. 11, every four elements), the azimuth resolution is not degraded, because the reception aperture is not changed. However, grating lobes occur, because the element pitch is fourfold.

Therefore, in the second embodiment, the arrangement of the ultrasonic elements whose outputs are used by the reception beam former 603 is determined for each reception in such a manner that all the ultrasonic elements of the ultrasonic element array 100 are used for generating phase outputs for one time or more by performing N times of reception equal to the addition number N. Alternatively, a configuration is provided in which after performing reception for all transmissions, the ultrasonic elements of the ultrasonic element array 100 in a predetermined range are used for one time or more.

Thus, even though the number (S) of the ultrasonic elements used for generating phase outputs is decreased in priority of imaging speed and reduction in stripes, the occurrence of grating lobes can be prevented, and reduction in resolution can be reduced.

Figure 12:
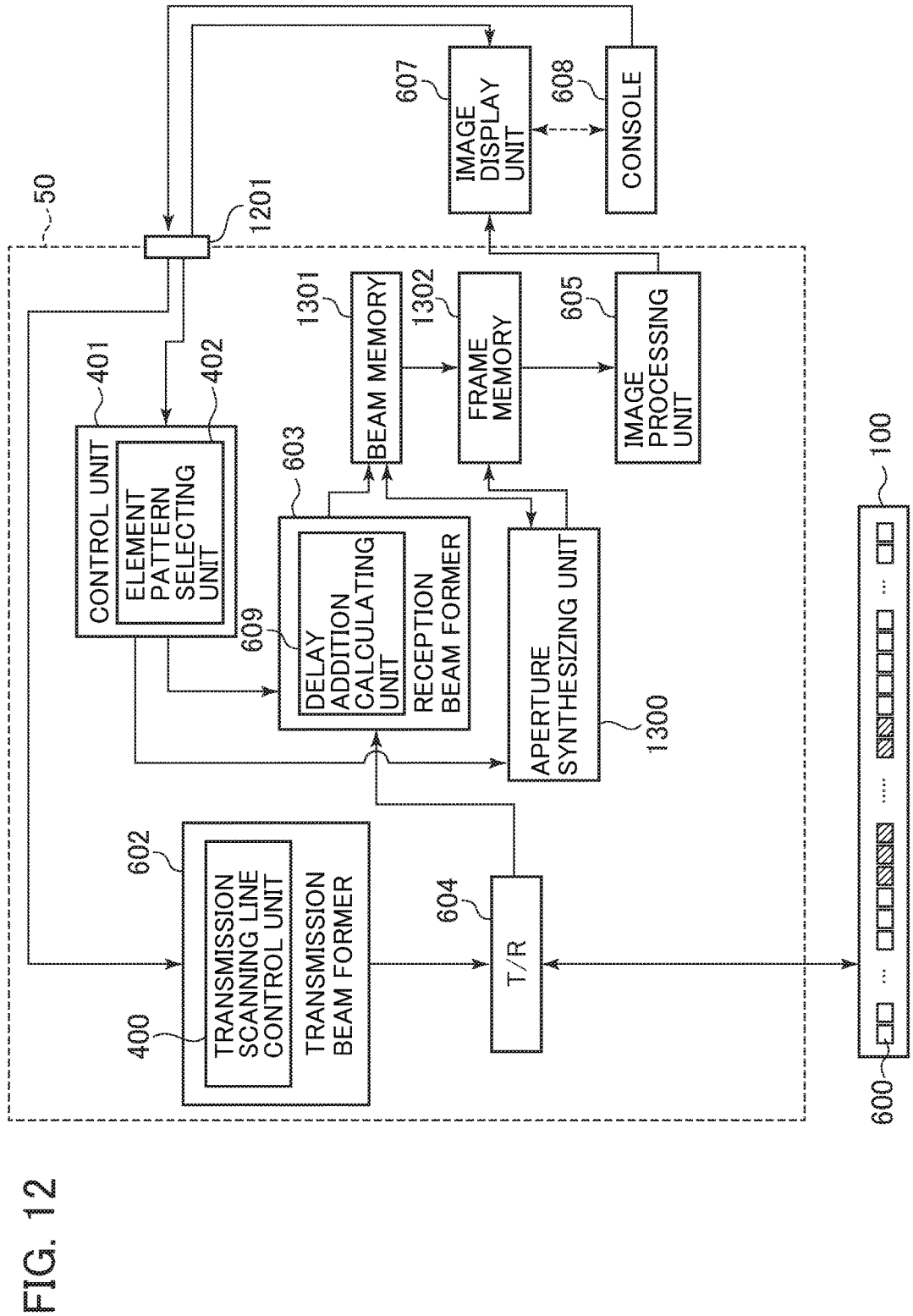
FIG. 12 is a block diagram of the configuration of an ultrasonic diagnostic apparatus according to a second embodiment.

Referring to FIG. 12, the ultrasound imaging apparatus according to the second embodiment of the present invention will be further described.

As illustrated in FIG. 12, the ultrasound imaging apparatus according to the second embodiment has a configuration similar to the configuration of the ultrasonic diagnostic apparatus according to the first embodiment (FIG. 4). However, the ultrasound imaging apparatus according to the second embodiment is different from the first embodiment in that an element pattern selecting unit 402 is disposed in the control unit 401. The element pattern selecting unit 402 selects the pattern of the arrangement of the ultrasonic elements for use in phasing.

Figure 13:
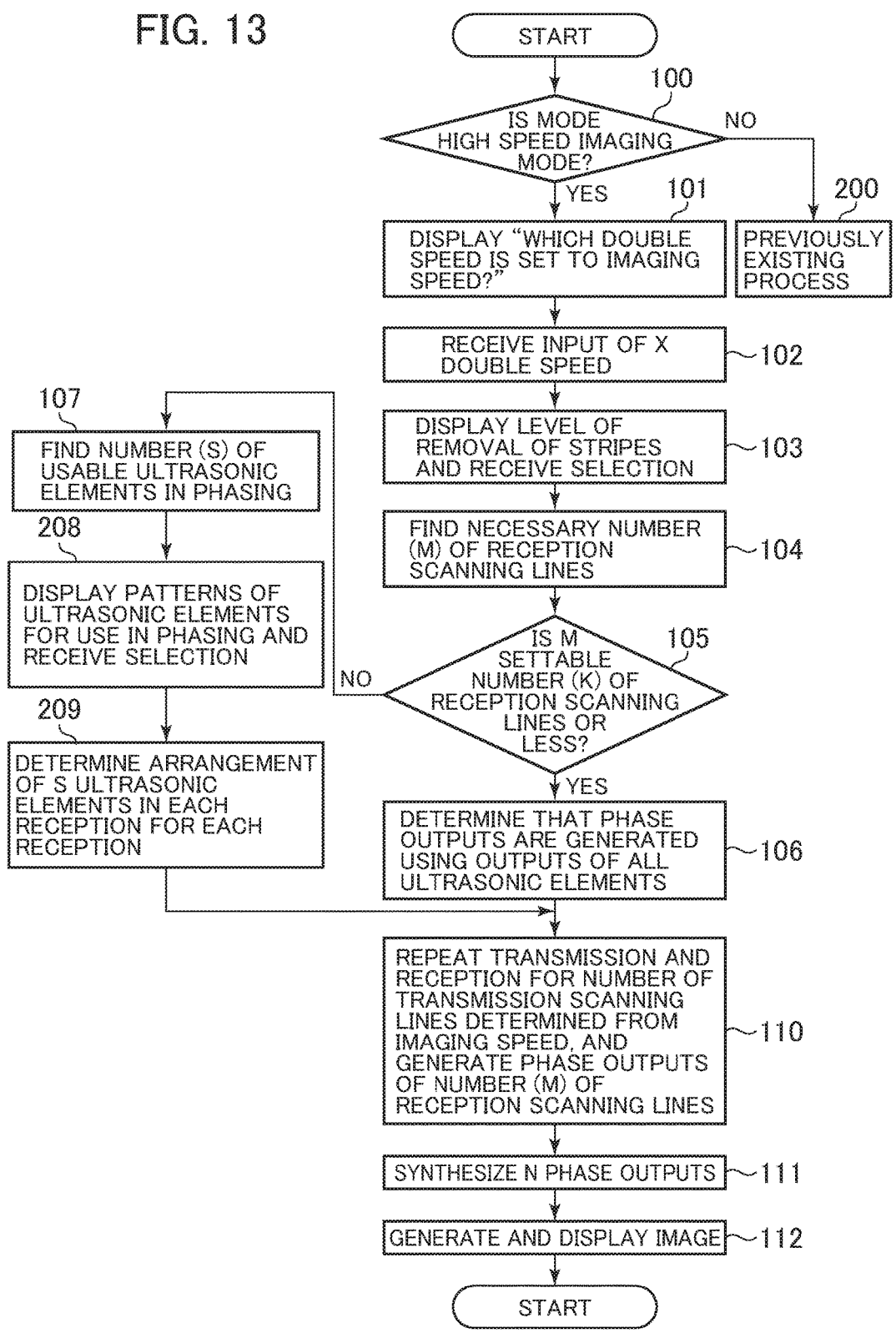
FIG. 13 is a flowchart of the operation of the ultrasound imaging apparatus according to the second embodiment.

The operation of the ultrasound imaging apparatus according to the second embodiment will be described with reference to a flowchart in FIG. 13. The flow in FIG. 13 is similar to the flow in FIG. 6 of the first embodiment. However, the flow in FIG. 13 is different from the flow in FIG. 6 in that Steps 208, 209 are provided instead of Steps 108, 109 in FIG. 6. In Steps 100 to 107, the processes are performed similarly to the first embodiment. In the case where in Step 105, the necessary number M of the reception scanning lines exceeds the settable number (K), in Step 107, the number (S) of the ultrasonic elements usable in phasing is found. This allows a decrease in the number of the ultrasonic elements used for generating phase outputs, and a decrease in the amount of arithmetic operation. Consequently, the phase outputs of the necessary number M of the transmission scanning lines can be operated within the transmission time interval. At this time, grating lobes occur depending on the arrangement of S elements of the ultrasonic elements of the ultrasonic element array 100. Thus, in the second embodiment, the arrangement of the ultrasonic elements used for generating phase outputs is determined for each reception in such a manner that all the ultrasonic elements of the ultrasonic element array 100 or the ultrasonic elements in a predetermined range are used for generating phase outputs for one time or more. Accordingly, the occurrence of grating lobes is reduced.

Specifically, the element pattern selecting unit 402 of the control unit 401 displays a plurality of types of ultrasonic element patterns for reducing grating lobes on an image display unit 607, and receives a selection from a user. Here, the element pattern selecting unit displays four types of patterns in total in FIGS. 14 to 17 as selectable patterns.

Figure 14:
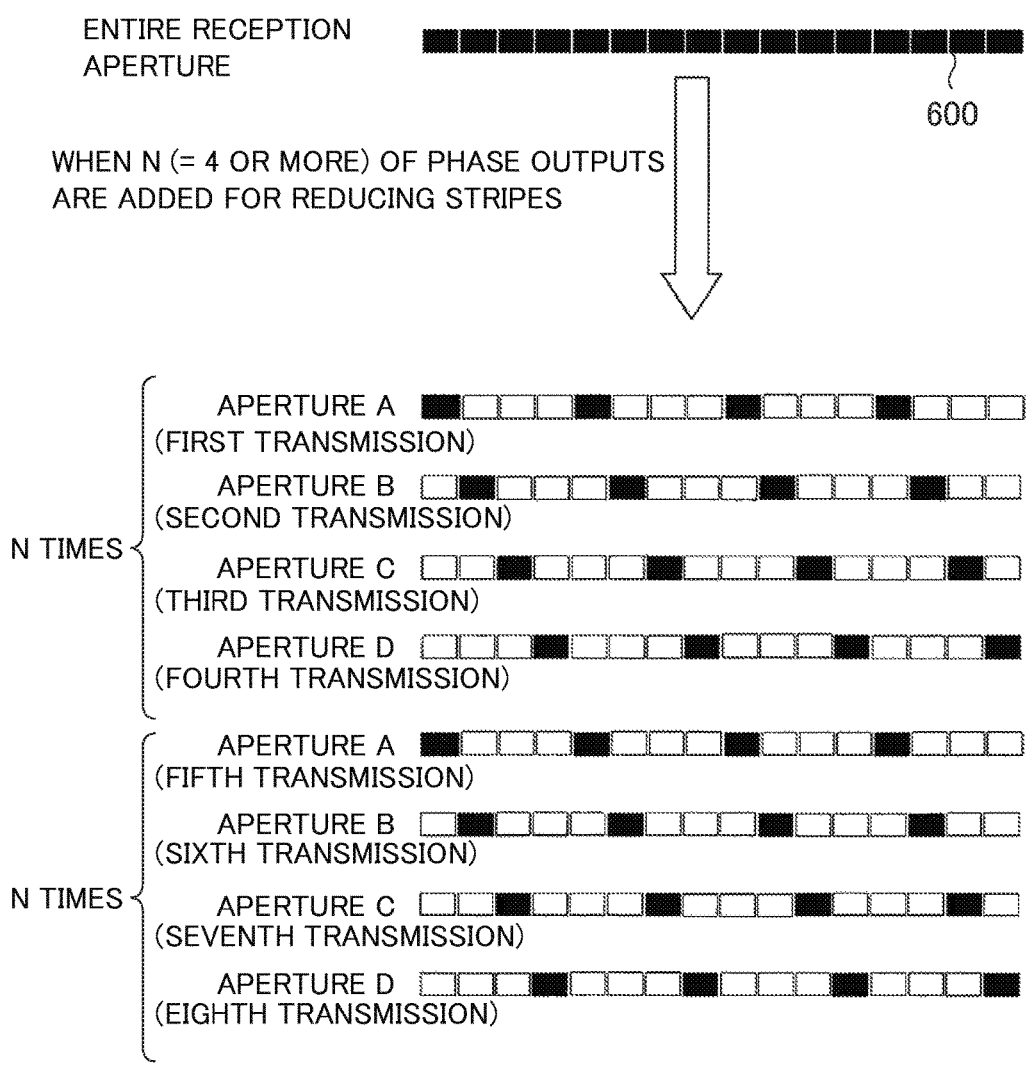
FIG. 14 is an illustration of element selection patterns (fixed intervals) displayed in Step 208 in the second embodiment.

The pattern in FIG. 14 is a pattern in which the ultrasonic elements 600 used for generating phase outputs are selected at certain intervals, and the position of the ultrasonic element 600 to be selected is shifted by one element for each reception. For example, in the case where the number (S) of the usable ultrasonic elements 600 in phasing found in Step 107 is 25% of all the ultrasonic elements 600, the ultrasonic element 600 is selected at a ratio of one to four ultrasonic elements 600. Thus, in the case where the addition number (N) corresponding to the level of reducing stripes selected in Step 103 is four or more, all the ultrasonic elements 600 are used for one time or more in phasing N phase outputs to be added in Step 111. Consequently, the phase outputs after subjected to aperture synthesis in Step 111 are obtained using all the ultrasonic elements 600, allowing reduction in the occurrence of grating lobes.

The element selection pattern in FIG. 14 will be further described. In the case where the user selects the pattern in FIG. 14 in Step 208, the element pattern selecting unit 402 determines the arrangement in Step 209 in such a manner that the number (S) of the ultrasonic elements 600, which is found in Step 107, are equally arraigned and the ultrasonic elements 600 are shifted by one element for every reception. For example, as illustrated in FIG. 14, in the case where the total number of the ultrasonic elements 600 is 16 and S elements of ultrasonic elements 600 are 25% of all the ultrasonic elements 600, the element pattern selecting unit 402 determines that in reception for the first time transmission, only the first, fifth, ninth, and thirteenth ultrasonic elements 600 (aperture A) from the left are used for operating the phase outputs. The element pattern selecting unit 402 determines that in reception for the second time transmission, only the second, sixth, tenth, and fourteenth ultrasonic elements 600 (aperture B) from the left are used as one element is sifted. Similarly, the element pattern selecting unit 402 determines that in reception for the third time transmission, only the third, seventh, eleventh, and fifteenth ultrasonic elements 600 (aperture C) from the left are used, and in reception for the fourth time transmission, only fourth, eighth, twelfth, and sixteenth ultrasonic elements 600 (aperture D) from the left are used. Similarly, in reception for the fifth time transmission and later, the ultrasonic elements 600 are arranged as one ultrasonic element 600 is shifted. Note that, in the example in FIG. 14, the number (S elements) of the ultrasonic elements 600 found in Step 107 is just one-fourth of all the ultrasonic elements, and thus the element is selected at a ratio of one to four ultrasonic elements 600. However, in some cases, the number of all the ultrasonic elements 600 is not the number S, which is an integer, and it is not possible to select the ultrasonic elements 600 at a ratio of one to some ultrasonic elements 600 for all the elements. In this case, a configuration only has to be provided, in which after the ultrasonic elements 600 are selected at a ratio of one to some ultrasonic elements 600 in Step 209, some ultrasonic elements 600 of the ultrasonic element array 100 at given positions are additionally selected. It is preferable to use as many of the ultrasonic elements to be selected as possible for improving the resolution of images and reducing artifacts.

In Step 110, transmission and reception are repeated for the set number of times, the phase outputs of M lines of the reception scanning lines are obtained in Step 209 only using the selected ultrasonic elements 600 for each reception, and then the phase outputs are stored on the beam memory 1301. The phase outputs stored on the beam memory 1301 obtained from the selected ultrasonic elements 600 are at coarse pitches. When images are generated as the pitches are unchanged, grating lobes occur. However, in the embodiment, N phase outputs are added (synthesized) for reducing stripes in Step 111. Thus, the phase outputs of all the ultrasonic elements (the total apertures=aperture A+aperture B+aperture C+aperture D) can be used for generating images. Consequently, grating lobes are canceled to prevent grating lobes from occurring.

Thus, effects are obtained, in which the number of the ultrasonic elements 600 used for operating the phase outputs is reduced, the imaging speed is maintained at high speed, and resolution is not degraded (grating lobes are prevented from occurring), while synthesizing N phase outputs for reducing stripes.

Figure 15:
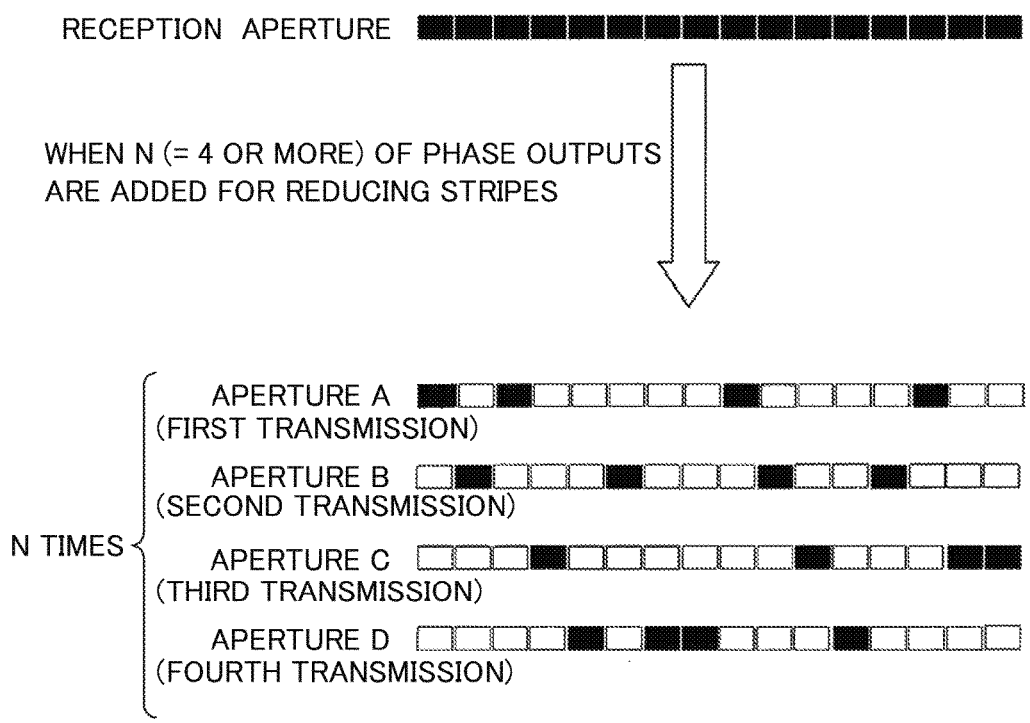
FIG. 15 is an illustration of element selection patterns (random) displayed in Step 208 in the second embodiment.

On the other hand, the pattern in FIG. 15 is a pattern in which the ultrasonic elements 600 used for generating phase outputs are determined in such a manner that S elements of ultrasonic elements 600 are randomly selected for each reception. However, all the ultrasonic elements 600 are to be selected for one time or more in N times of reception.

Figure 16:
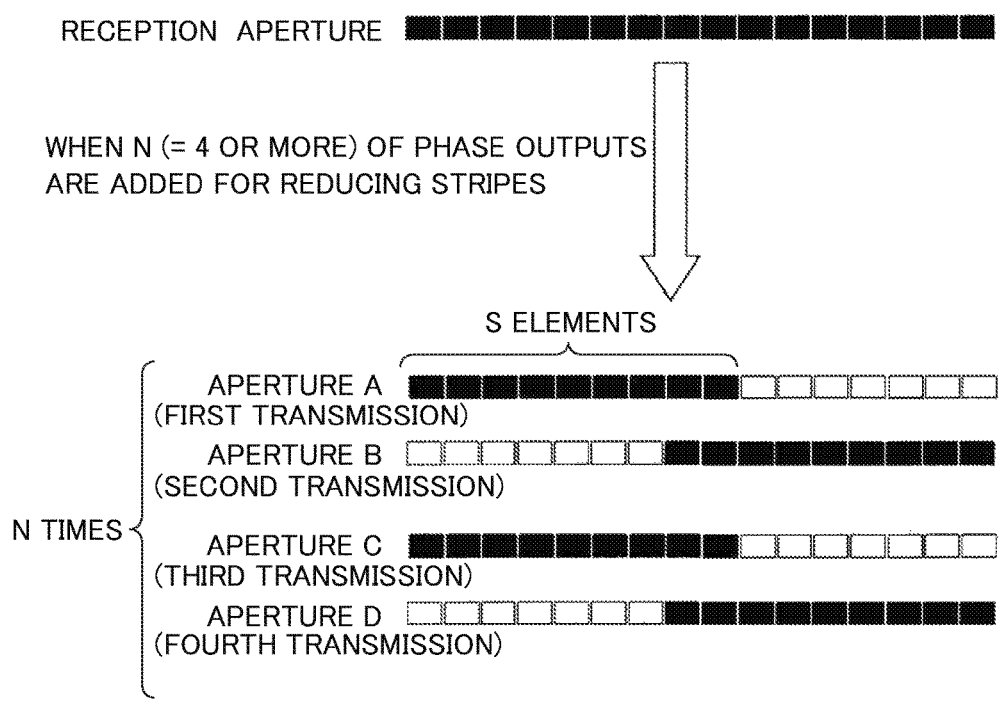
FIG. 16 is an illustration of another example of element selection patterns displayed in Step 208 in the second embodiment.

The pattern in FIG. 16 is a pattern in which S elements of the ultrasonic elements are arranged alternately from the left and right sides for each reception in such a manner that S elements of the ultrasonic elements 600 used for generating phase outputs are selected from the left end of the ultrasonic element array 100 in the first time reception, and S elements of the ultrasonic elements 600 are selected from the right end in the second time reception. In the case where S elements are one-half of all the ultrasonic elements, this pattern is preferable because all the ultrasonic elements 600 are surely selected for one time or more in N times of reception. In the case where S elements are less than one-half of all the ultrasonic elements, a pattern is adopted in which the position to be selected is sequentially shifted in such a manner that in the first time reception, S elements of the ultrasonic elements 600 are selected from the left end of the ultrasonic element array 100, and in the second time reception, S elements of the ultrasonic elements 600 are selected from the ultrasonic element 600 located on the right end of the S elements of the ultrasonic elements 600 selected in the first time. Thus, all the ultrasonic elements can be selected for one time or more in order of N times.

Figure 17:
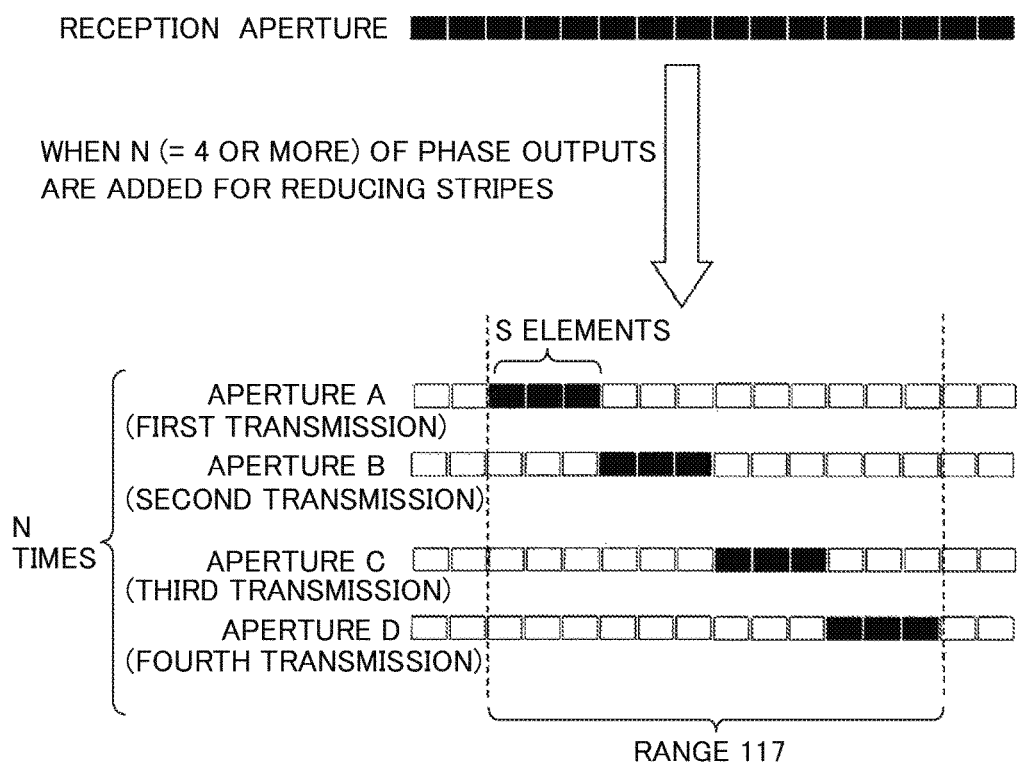
FIG. 17 is an illustration of still another example of element selection patterns displayed in Step 208 in the second embodiment.

The pattern in FIG. 17 is a pattern in which the arrangement of the ultrasonic elements 600 used for generating the phase outputs is determined for each reception in such a manner that ultrasonic elements in a predetermined range 117 are used for generating phase outputs for one time or more. For the predetermined range 117, it is desirable to set the range to a range N times S or less. Thus, the ultrasonic elements 600 in the range 117 are sequentially selected for every S elements in N times of reception. Consequently, all the ultrasonic elements in the range 117 can be selected for one time or more. For a method of selecting the ultrasonic elements 600 in the range 117, a pattern can be selected, as illustrated in FIG. 17, in which the position to be selected is sequentially shifted in such a manner that in the first time reception, S ultrasonic elements are selected from the left end of the range 117, and in the second time reception, S ultrasonic elements are selected from the right end of the S elements of the ultrasonic elements selected in the first time. Other than this method, the ultrasonic elements can also be selected in the range 117 by the patterns in FIG. 14 to 16.

In the case where the operator selects any one pattern in FIGS. 15 to 17 in Step 208, similarly in the pattern in FIG. 14, the element pattern selecting unit 402 selects the ultrasonic elements for each reception in Step 209 as illustrated in FIGS. 15 to 17. In Step 110, the reception beam former 603 generates the phase outputs using the outputs of the ultrasonic elements selected in Step 209 for each reception, and the phase outputs are stored on the beam memory 1301. The aperture synthesizing unit 1300 reads N phase outputs out of the beam memory 1301 at each received focal point, and adds the phase outputs.

Thus, in the patterns in FIGS. 15 to 16, the aperture synthesizing unit 1300 adds N phase outputs in Step 111. Thus, the outputs of all the ultrasonic elements 600 are used. Consequently, similarly to the pattern in FIG. 14, the effect is obtained, in which the resolution is not degraded while decreasing the number of the ultrasonic elements 600 used for operating the phase outputs and maintaining the imaging speed at high speed. On the other hand, in the pattern in FIG. 17, the outputs of all the ultrasonic elements in the range 117 of the entire ultrasonic elements are used, causing the resolution to be decreased more or less as compared with the pattern in FIG. 14. However, the imaging speed can be maintained at high speed while reducing the number of the ultrasonic elements 600 used for operating the phase outputs.

As described above, two embodiments according to the present invention are described. The foregoing embodiments are merely all exemplifications, which do not limit the scope of the present invention.

This embodiment is applied not only to the ultrasonic element array 100 having the ultrasonic elements 600 linearly arrayed but also to an ultrasonic element array having the ultrasonic elements 600 two-dimensionally arrayed of course. For example, FIG. 18 is a pattern of selecting ultrasonic elements in the case where the pattern in FIG. 14 is applied to a two-dimensional ultrasonic element array. As illustrated in FIG. 18, the pattern in FIG. 14 is applied to a short axis direction as well as a long axis direction. Consequently, the resolution is not degraded (the occurrence of grating lobes is prevented) in either of the short axis and long axis directions.

LIST OF REFERENCE SIGNS

10 . . . Transmission beam
11 . . . Received beam
30 . . . Reflecting object
27 . . . Boundary at which stripes appear in an ultrasound image
50 . . . Ultrasound imaging apparatus
100 . . . Ultrasonic element array
400 . . . Transmission scanning line control unit
401 . . . Control unit
600 . . . Ultrasonic element
602 . . . Transmission beam former
603 . . . Reception beam former
604 . . . Transmission/reception switching unit (T/R)
605 . . . Image processing unit 607 . . . Image display unit
608 . . . Console
609 . . . Delay addition calculating unit
1201 . . . Input/output port (receiving unit)
1300 . . . Aperture synthesizing unit
1301 . . . Beam memory
1302 . . . Frame memory

The invention claimed is:

1. An ultrasound imaging apparatus comprising:
an ultrasonic element array having a plurality of ultrasonic elements arrayed along a predetermined direction, the plurality of ultrasonic elements transmitting ultrasonic waves to an imaging area of a test object and receiving ultrasonic waves reflected off the test object;
a transmission beam former, comprising a transmission scanning line control unit, that sequentially transmits signals causing transmission beams to be transmitted from the ultrasonic element array along a plurality of transmission scanning lines set in the imaging area of the test object;
a reception beam former, comprising a delay addition calculating unit, that sets a plurality of reception scanning lines for each of the transmission beams and generates signals, the signals being generated by phasing and adding received outputs of the ultrasonic elements via the delay addition calculating unit, at a plurality of received focal points on the respective reception scanning lines;
a beam memory, which stores a plurality of phase outputs corresponding to each of the plurality of reception scanning lines generated by the reception beam former;
an aperture synthesizing unit that adds a plurality of phase outputs obtained from reflected ultrasonic waves of the transmission beams, including the stored plurality of phase outputs from the beam memory, which are different, at the received focal points, which are the same;
a frame memory which stores a phase output generated by the aperture synthesizing unit;
an image processing unit which reads the phase output stored on the frame memory and generates an image of the imaging area;
an image display unit which displays the generated image;
a receiving unit that receives an instruction to perform a high speed imaging mode from an operator;
a transmission/reception switching unit which transmits the signals from the transmission beam former to the ultrasonic element array and receives signals from the ultrasonic element array; and
a control unit,
wherein when the receiving unit receives an instruction to perform a high speed imaging mode, the transmission scanning line control unit determines intervals, corresponding to speed in the high speed imaging mode, between the plurality of transmission scanning lines, and the transmission beam former sequentially transmits the signals causing the transmission beams to be transmitted along the plurality of transmission scanning lines at the determined intervals corresponding to imaging speed in the high speed imaging mode;
the aperture synthesizing unit sets a number of the phase outputs to be added at each of the received focal points to a predetermined addition number (N) reducing occurrence of stripes on the image; and
in order to generate the addition number (N) of the phase outputs at each of the received focal points, the control unit finds a number (M) of the reception scanning lines, the number (M) set by the reception beam former, and the control unit notifies the reception beam former of the found number (M) of the reception scanning lines.

2. The ultrasound imaging apparatus according to claim 1, wherein when the number (M) of the reception scanning lines is a predetermined number (K) or less, the control unit causes the reception beam former to generate the phase outputs using outputs of all the ultrasonic elements of the ultrasonic element array.

3. The ultrasound imaging apparatus according to claim 1, wherein when the number (M) of the reception scanning lines exceeds a predetermined number (K), the control unit finds a number (S) of the ultrasonic elements usable for generating the phase outputs at the received focal points of the number (M) of the reception scanning lines at a transmission time interval of the transmission beams based on an operating capability of the reception beam former, and causes the reception beam former to generate the phase outputs using the received outputs of the found number of the ultrasonic elements.

4. The ultrasound imaging apparatus according to claim 3, wherein when the number (M) of the reception scanning lines exceeds a predetermined number (K), the control unit displays an indication on a display device for informing the operator of a possibility of a decrease in resolution.

5. The ultrasound imaging apparatus according to claim 3, wherein in the ultrasonic elements arrayed on the ultrasonic element array, the control unit determines an arrangement of the number (S) of the ultrasonic elements whose received outputs are used by the reception beam former, based on a predetermined pattern.

6. The ultrasound imaging apparatus according to claim 5, wherein the control unit determines an arrangement of the ultrasonic elements whose outputs are used by the reception beam former for each reception so that the reception beam former uses all the ultrasonic elements of the ultrasonic element array for generating phase outputs for one time or more in reception for N times of transmission equal to the addition number (N).

7. The ultrasound imaging apparatus according to claim 5, wherein the control unit determines an arrangement of the ultrasonic elements whose outputs are used by the reception beam former so that the reception beam former uses a predetermined number of the ultrasonic elements among all the ultrasonic elements of the ultrasonic element array for generating phase outputs for one time or more in reception for N times of transmission equal to the addition number (N).

8. The ultrasound imaging apparatus according to claim 5, wherein the control unit displays a plurality of types of predetermined patterns, receives a selection of a pattern by the operator through the receiving unit, and determines an arrangement of the ultrasonic elements using the received pattern as the predetermined pattern.

9. The ultrasound imaging apparatus according to claim 5, wherein the predetermined pattern is a pattern in which (S) elements of the ultrasonic elements whose outputs are used by the reception beam former are arranged at a certain interval along a direction of arranging the ultrasonic elements and the arrangement of the ultrasonic elements is shifted by one ultrasonic element for each reception.

10. The ultrasound imaging apparatus according to claim 5, wherein the predetermined pattern is a pattern in which (S) elements of the ultrasonic elements whose outputs are used by the reception beam former are randomly arranged along a direction of arranging the ultrasonic elements.

11. The ultrasound imaging apparatus according to claim 1,
wherein the receiving unit receives a level of reducing the stripes from the operator; and
the control unit sets the addition number (N) suitable for the reducing level received by the receiving unit, and finds the number (M) of the reception scanning lines suitable for the set addition number (N).

12. The ultrasound imaging apparatus according to claim 1,
wherein the control unit includes a table showing a relationship between the imaging speed, the addition number (N) of the phase outputs, and the number (M) of the reception scanning lines found in advance; and
with reference to the table, the control unit finds the number (M) of the reception scanning lines corresponding to the imaging speed and the addition number (N).

13. An ultrasound imaging apparatus comprising:
an ultrasonic element array having a plurality of ultrasonic elements arrayed along a predetermined direction, the plurality of ultrasonic elements transmitting ultrasonic waves to an imaging area of a test object and receiving ultrasonic waves reflected off the test object;
a transmission beam former, comprising a transmission scanning line control unit, that sequentially transmits signals causing transmission beams to be transmitted from the ultrasonic element array along a plurality of transmission scanning lines set in the imaging area of the test object;
a reception beam former, comprising a delay addition calculating unit, that sets a plurality of reception scanning lines for each of the transmission beams and generates signals, the signals being generated by phasing and adding received outputs of the ultrasonic elements via the delay additional calculating unit, at a plurality of received focal points on the respective reception scanning lines;
a beam memory, which stores a plurality of phase outputs corresponding to each of the plurality of reception scanning lines generated by the reception beam former;
an aperture synthesizing unit that adds a plurality of phase outputs obtained from reflected ultrasonic waves of the transmission beams, including the stored plurality of phase outputs from the beam memory, which are different, at the received focal points, which are the same;
a frame memory which stores a phase output generated by the aperture synthesizing unit an image processing unit which reads the phase output stored on the frame memory and generates an image of the imaging area;
an image display unit which displays the generated image;
a receiving unit that receives an instruction to perform a high speed imaging mode from an operator;
a transmission/reception switching unit which transmits the signals from the transmission beam former to the ultrasonic element array and receives signals from the ultrasonic element array; and
a control unit,
wherein: when the receiving unit receives an instruction to perform a high speed imaging mode, the aperture synthesizing unit sets a number of the phase outputs to be added at each of the received focal points to a predetermined addition number (N) reducing occurrence of stripes on the image; and
the control unit determines an arrangement of the ultrasonic elements whose outputs are used by the reception beam former for each reception so that the reception beam former uses all of the ultrasonic elements of the ultrasonic element array or the ultrasonic elements in a predetermined range for generating phase outputs for one time or more in reception for N times of transmission equal to the addition number (N).

14. The ultrasound imaging apparatus according to claim 13,
wherein when the receiving unit receives an instruction to perform a high speed imaging mode, the transmission scanning line control unit determines intervals, corresponding to speed in the high speed imaging mode, between the plurality of transmission scanning lines, and the transmission beam former sequentially transmits signals causing transmission beams to be transmitted along the plurality of transmission scanning lines at the determined intervals corresponding to imaging speed in the high speed imaging mode; and
in order to generate the addition number (N) of the phase outputs at each of the received focal points, the control unit finds a number (M) of the reception scanning lines, the number (M) set by the reception beam former, and the control unit notifies the reception beam former of the found number (M) of the reception scanning lines.

* * * * *